(12) United States Patent
Agada et al.

(10) Patent No.: US 11,484,712 B2
(45) Date of Patent: Nov. 1, 2022

(54) WEARABLE STOCHASTIC GALVANIC STIMULATION DEVICE

(71) Applicant: Temple University-Of The Commonwealth System of Higher Education, Philadelphia, PA (US)

(72) Inventors: Peter Igoche Agada, Philadelphia, PA (US); John Jeka, Philadelphia, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 292 days.

(21) Appl. No.: 15/994,028

(22) Filed: May 31, 2018

(65) Prior Publication Data

US 2018/0345016 A1 Dec. 6, 2018

Related U.S. Application Data

(60) Provisional application No. 62/513,209, filed on May 31, 2017.

(51) Int. Cl.
| | |
|---|---|
| A61N 1/36 | (2006.01) |
| A61N 1/02 | (2006.01) |
| A61N 1/04 | (2006.01) |
| A61B 5/11 | (2006.01) |
| A61B 5/00 | (2006.01) |
| A61N 1/378 | (2006.01) |

(52) U.S. Cl.
CPC .......... *A61N 1/36036* (2017.08); *A61B 5/002* (2013.01); *A61B 5/0022* (2013.01); *A61B 5/1116* (2013.01); *A61B 5/4023* (2013.01); *A61B 5/6803* (2013.01); *A61N 1/025* (2013.01); *A61N 1/0476* (2013.01); *A61N 1/0484* (2013.01); *A61N 1/36031* (2017.08); *A61N 1/3787* (2013.01); *A61B 2560/0214* (2013.01); *A61B 2562/0219* (2013.01); *A61B 2562/0223* (2013.01)

(58) Field of Classification Search
CPC .. A61B 5/6803; A61B 5/024; A61N 1/36036; A61N 1/0456
See application file for complete search history.

(56) References Cited

U.S. PATENT DOCUMENTS

| | | |
|---|---|---|
| 4,331,163 A | 5/1982 | Nomura |
| 4,558,703 A | 12/1985 | Mark |
| 6,546,291 B2 | 4/2003 | Merfeld |
| 8,355,788 B2 | 1/2013 | Mechlenburg |
| 2012/0277835 A1* | 11/2012 | Della Santina .......... A61N 1/36 607/62 |
| 2018/0133431 A1* | 5/2018 | Malchano ............ A61B 5/4836 |
| 2019/0223747 A1* | 7/2019 | Chou ..................... A61B 5/681 |

* cited by examiner

*Primary Examiner* — Michael J D'Abreu
(74) *Attorney, Agent, or Firm* — Riverside Law LLP

(57) ABSTRACT

The present invention provides in part wearable devices for balance control. The wearable devices are capable of non-invasively monitoring and stimulating the wearer's vestibular system such that it produces postural responses. The wearable devices deliver low levels of electrical current to the vestibular system of a user to maintain balance. In one example, the wearable device is in the form of a pair of glasses.

18 Claims, 5 Drawing Sheets

WEARABLE STOCHASTIC GALVANIC STIMULATION DEVICE

CROSS-REFERENCE TO RELATED APPLICATIONS

This application claims priority to U.S. Provisional Patent Application No. 62/513,209 filed May 31, 2017, the contents of which are incorporated by reference herein in its entirety.

BACKGROUND OF THE INVENTION

The vestibular system operates as a biological inertial sensor capable of detecting both angular and linear rate changes of a person's head in space. These inertial parameters are detected by deflections of hair cells within the sensory organs located in the inner ear, which initiates a transmission of afferent (towards the brain) neural signals along vestibular pathways towards the central nervous system, where they are integrated to form an absolute reference system of the head and body. This absolute reference when combined with other sensory signals from the visual and somatosensory system is paramount to executing the optimal control of upright balance while performing volitional tasks during stance and locomotion. Approximately 30-35% of older adults suffer from vestibular dysfunction brought on by the loss of hair cells, which frequently leads to an increased perception of disequilibrium and injurious falls. Injury statistics data from community dwelling centers further highlight the issue of falls among seniors, as some have shown that 80% of the members that experienced a fall suffered from vestibular impairment. Treating falls in the United States costs Medicare approximately $31 billion annually; the introduction of additional older adults from the aging baby boomer population over the next 15 years is projected to double the costs.

There is a need in the art for a device capable of monitoring and improving vestibular function. The present invention satisfies this need.

SUMMARY OF THE INVENTION

In one aspect, the present invention relates to a galvanic vestibular stimulation device, comprising: a glasses frame, temples, and temple tips; one or more electrodes; one or more wireless transceivers; one or more accelerometers; one or more gyroscopes; one or more magnetometers; one or more processors; and one or more batteries.

In one embodiment, the one or more electrodes are positioned within the temple tips. In one embodiment, the temple tips are curved inwards towards each other. In one embodiment, the one or more electrodes deliver stochastic electrical stimulation to a user's skin near the user's mastoid process to enhance postural response.

In one embodiment, the device sends, stores, and receives signals from cloud storage. In one embodiment, the device sends, stores, and receives signals to an onboard non-transitory computer-readable storage media.

In one embodiment, one or more of the accelerometers, gyroscopes, and magnetometers communicate with the one or more processors to send information relating to the device's speed, acceleration, orientation, location, and direction. In one embodiment, the one or more processors adjusts the level of the stimulation to the one or more electrodes to increase, decrease, or maintain electrode firing rate based on the received information.

In one embodiment, the one or more wireless transceivers are selected from the group consisting of: Bluetooth transceiver, WiFi transceiver, near field communication transceiver, and mobile transceiver.

In one embodiment, the one or more batteries are rechargeable. In one embodiment, the one or more batteries are removable. In one embodiment, the device further comprises one or more inductive charging coils. In one embodiment, the device further comprises one or more corrective lenses or non-corrective lenses.

In another aspect, the present invention relates to a system for galvanic vestibular stimulation, comprising: a glasses frame, temples, temple tips, one or more electrodes, one or more wireless transceivers, one or more accelerometers, one or more gyroscopes, one or more magnetometers, one or more processor, and one or more batteries; and one or more non-transitory computer-readable media with instructions stored thereon; wherein the instructions, when executed by the one or more processors, determine speed, acceleration, orientation, location, and direction of the glasses frame and modulates a level of stimulation at the one or more electrodes.

In one embodiment, the one or more electrodes are positioned within the temple tips. In one embodiment, the one or more electrodes deliver stochastic electrical stimulation to a user's skin near the user's mastoid process to enhance postural response.

In one embodiment, the one or more wireless transceivers are selected from the group consisting of: Bluetooth transceiver, WiFi transceiver, near field communication transceiver, and mobile transceiver.

In one embodiment, the one or more batteries are rechargeable or removable. In one embodiment, the system further comprises one or more inductive charging coils. In one embodiment, the system further comprises corrective lenses or non-corrective lenses.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
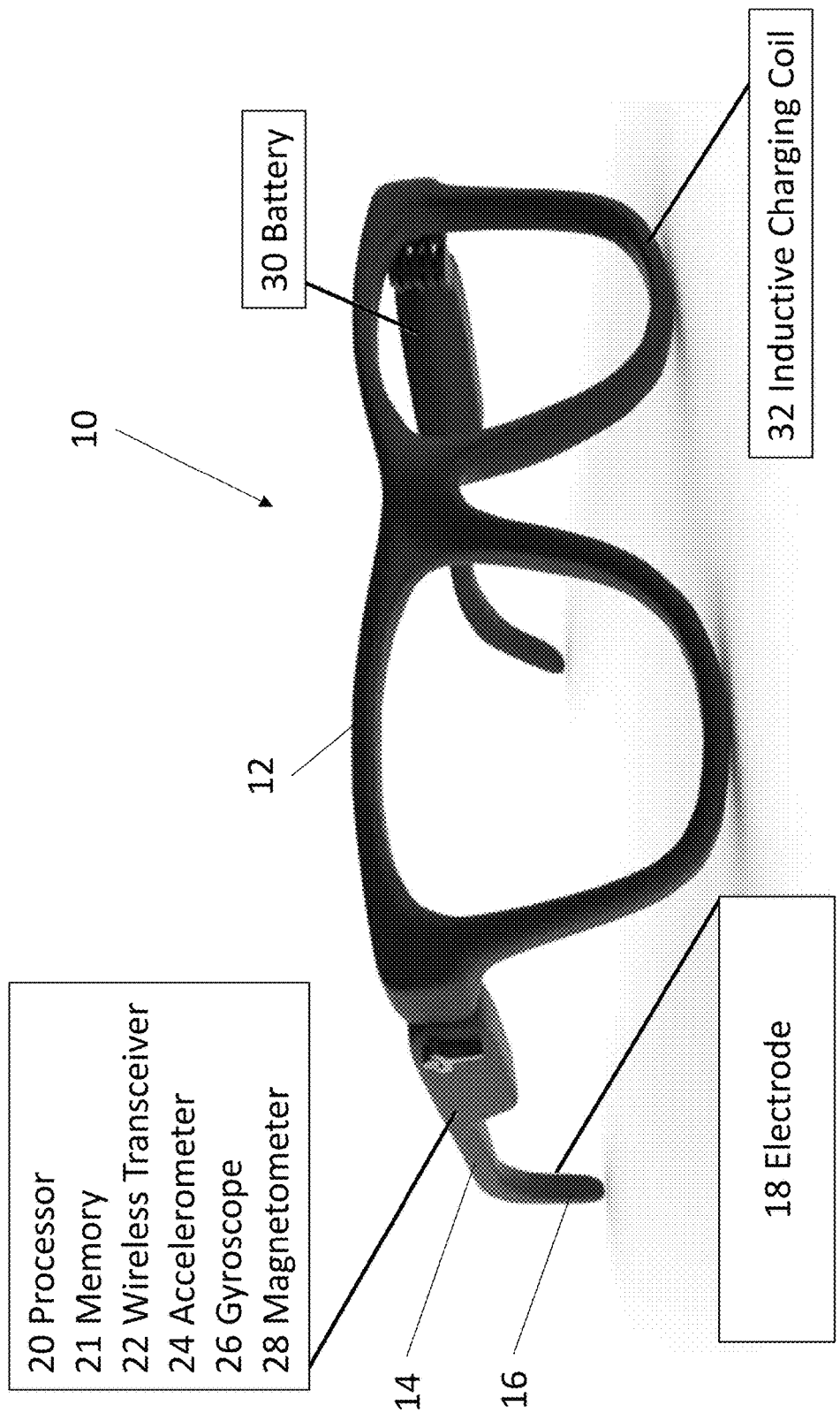
FIG. 1 depicts an exemplary stochastic galvanic stimulation device.

The present invention provides in part wearable devices for balance control. The wearable devices are capable of non-invasively monitoring and stimulating the wearer's vestibular system such that it produces postural responses. The wearable devices deliver low levels of electrical current to the vestibular system of a user to maintain balance. In one example, the wearable device is in the form of a pair of glasses.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Any methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Stochastic Galvanic Stimulation Device

The present invention provides in part wearable devices for balance control and monitoring during upright stance and locomotion. The devices are useful for rehabilitation purposes for older adults experiencing balance disequilibrium during stance and locomotion due to vestibular dysfunction. The devices are capable of delivering low levels of electrical current to a user's vestibular system to enhance the user's perception and integration of gravicentric sensory information. In certain embodiments, the devices are capable of modulating the transmission or firing rate of the vestibular afferent signals through low levels of stochastic transcutaneous electrical current to the user to enhance the user's postural response in stance and locomotion.

In one aspect, the wearable device has the form of eyewear. Referring now to FIG. 1, an exemplary device 10 is depicted. Device 10 comprises frame 12 and temples (arms) 14 with temple (arm) tips 16. As will be understood by those having skill in the art, the components of device 10 can have any suitable shape or form. For example, frame 12 and temples 14 can be constructed from any suitable material such as a metal, a plastic, a polymer, or any combination thereof. Frame 12 can be provided with or without lenses. For example, if a user does not require corrective lenses, frame 12 can be lensless, or be fitted with non-prescription lenses, polarized lenses, ultraviolet-protective lenses, and the like. In other examples, if a user requires corrective lenses, frame 12 can be fitted with any corrective lens known in the art, including bifocals, trifocals, progressive lenses, and the like. In some embodiments, temples 14 include mounting points for side shields, such as in safety glasses. In some embodiments, temples 14 can be in the form of a component that wraps around a user's head, such as an elastic band similar to those employed in goggles. Temple tips 16 are positioned at the ends of temples 14 and can be rigid or flexible. In certain embodiments, temple tips 16 can be curved or directed inwards towards each other. In such a construction, temples 14 position temple tips 16 behind the ears of a user when worn, and the curvature of temple tips 16 press temple tips 16 against the skin of the user such that temple tips 16 are positioned snugly against the skin adjacent to the user's mastoid processes on both sides of the head.

Device 10 further comprises processor 20 and memory 21 electrically connected to electrode 18, wireless transceiver 22, accelerometer 24, gyroscope 26, magnetometer 28, and battery 30. Memory 21 can include one or more non-transitory computer-readable media. One or more electrode 18 can be embedded in at least one temple tip 16. As described elsewhere herein, temples 14 position temple tips 16 behind the ears of a user when worn, and the curvature of temple tips 16 press temple tips 16 against the skin adjacent to a user's mastoid process on either side of the head, thereby also pressing the one or more electrode 18 against the skin adjacent to a user's mastoid process on either side of the head. The one or more electrodes 18 are thereby positioned to deliver electrical stimulation to a user in the region of the mastoid processes. The one or more electrodes 18 can be provided in any arrangement suitable for galvanic vestibular stimulation. For example, in one embodiment, the electrodes 18 are arranged to deliver bilateral bipolar galvanic vestibular stimulation, wherein at least one electrode 18 is provided in one temple tip 14, and at least one electrode 18 is provided in the opposite temple tip 14. One temple tip 14 receiving cathodal stimulation induces a perceived sway, causing a balance correction in the opposite temple tip 14 receiving anodal stimulation, and balance maintenance may be achieved by switching stimulation polarity to alternate cathodal and anodal stimulation between the electrodes 18 in each of the temple tips 14. In another embodiment, the electrodes 18 are arranged to deliver unilateral galvanic vestibular stimulation, wherein at least one electrode 18 is provided in a single temple tip 14, and at least one additional electrode 18 is positioned at a location on the body remote from the mastoid processes. Similarly to the bilateral bipolar arrangement, a single temple tip 14 receiving cathodal stimulation induces a perceived sway in the direction of the single temple tip 14, causing a balance correction in the opposite direction, and balance maintenance may be achieved by switching stimulation polarity to alternate cathodal and anodal stimulation between the electrodes 18 in the single temple tip 14 and the remote electrodes 18. In another embodiment, the electrodes 18 are arranged to deliver bilateral monopolar galvanic stimulation, wherein at least one electrode 18 is provided in both temple tips 14, and at least one additional electrode 18 is positioned at a location on the body remote from the mastoid processes. In this manner, both temple tips 14 receiving cathodal stimulation induces a perceived forward sway, causing a balance correction in the opposite direction, and balance maintenance may be achieved by switching stimulation polarity to alternate cathodal and anodal stimulation between the electrodes 18 in the temple tips 14 and the remote electrodes 18.

Figure 2:
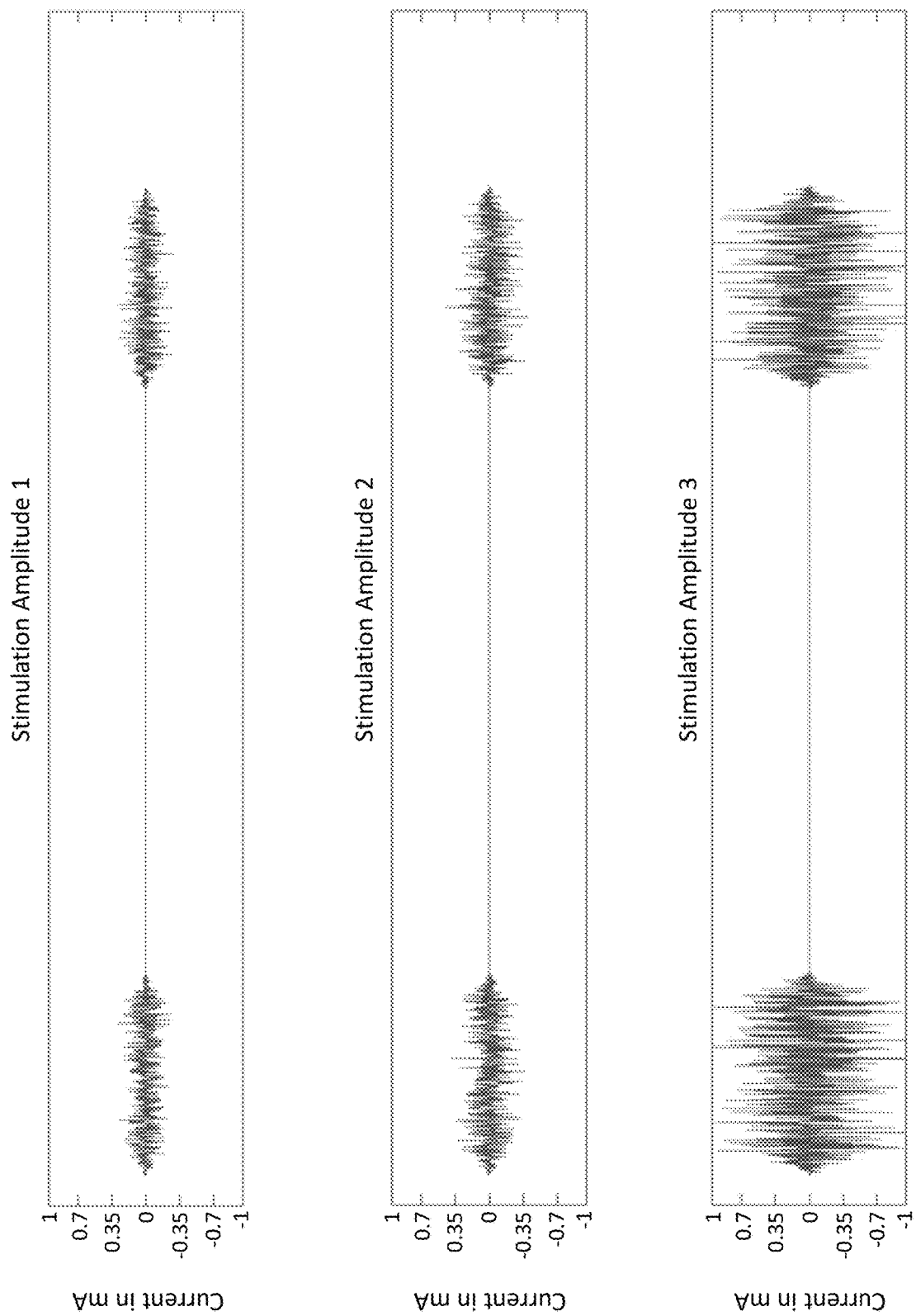
FIG. 2 depicts the ability of an exemplary device to have varied amplitude of stimulation for the vestibular system of a wearer of the device.
Figure 3:
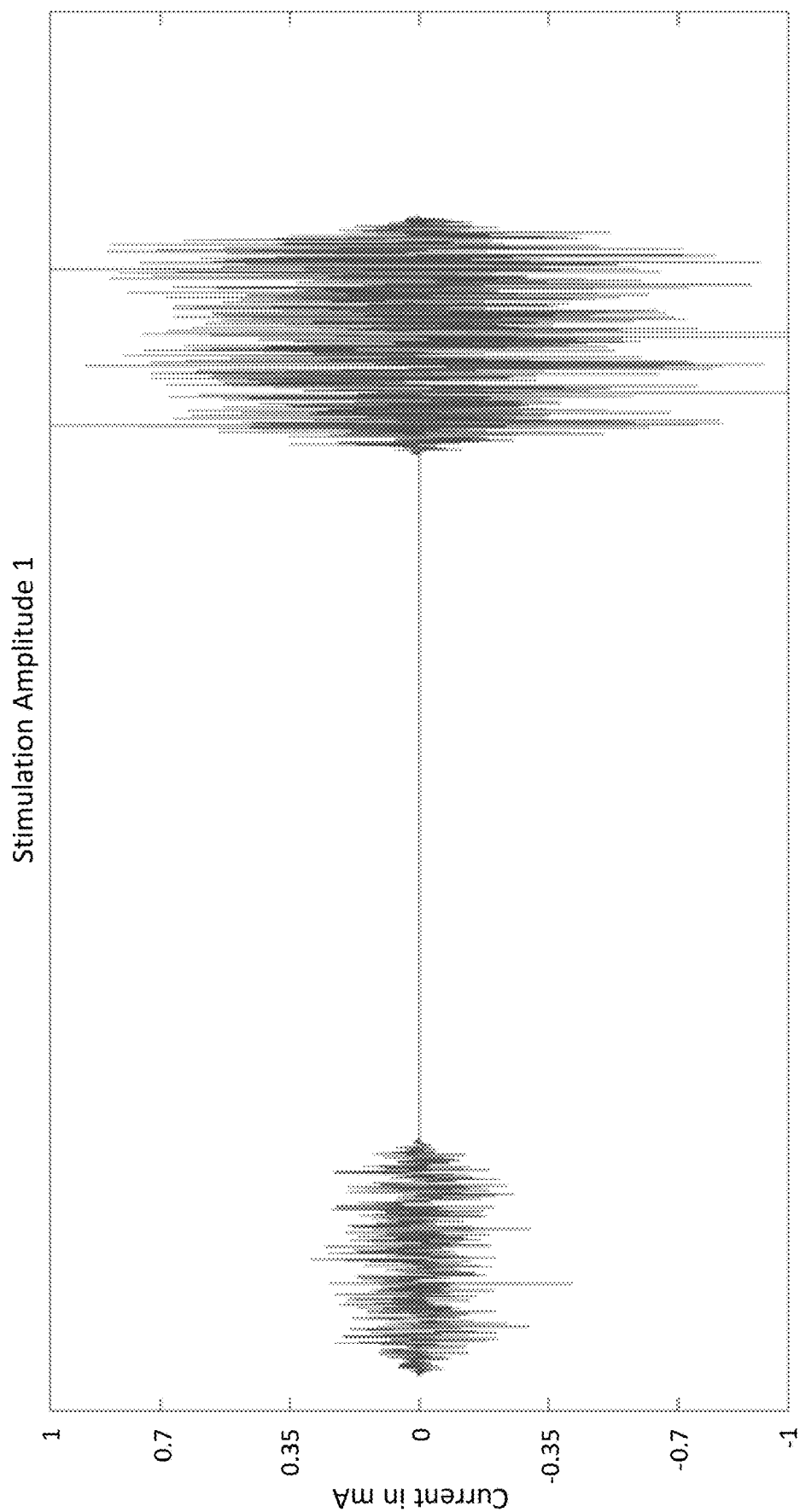
FIG. 3 depicts the ability of an exemplary device to have varied amplitude of stimulation between periods for the vestibular system of a wearer of the device.
Figure 4:
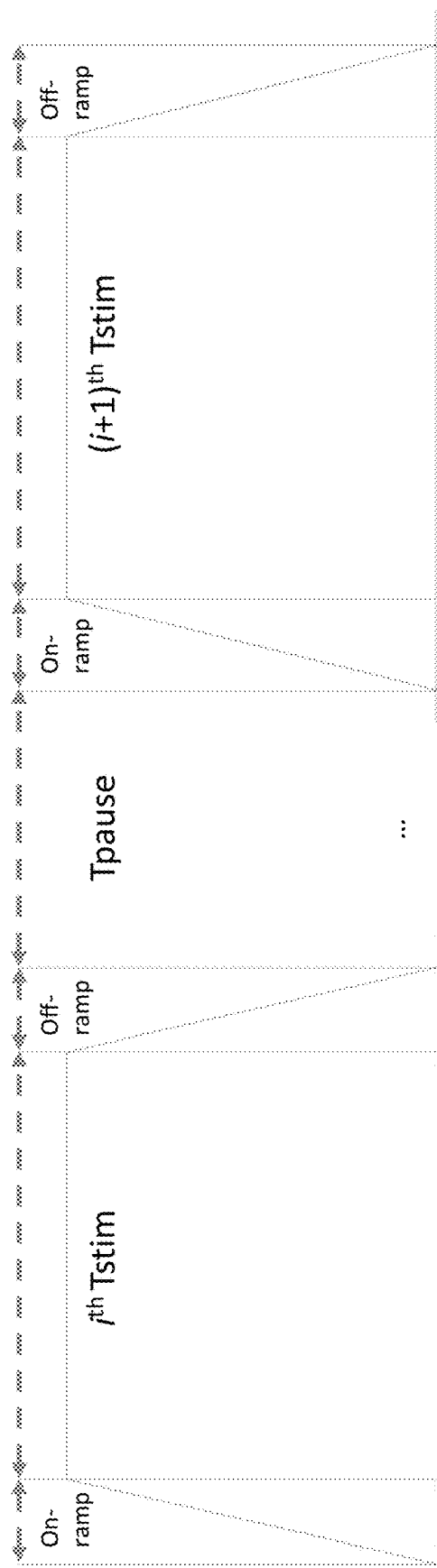
FIG. 4 depicts an exemplary stimulation pattern. On-ramp represents a configurable positive slope to control the power of the electrical stimulation when the device starts to increase its stimulation of the vestibular system. The duration of On-ramp can be between 1 and 60 seconds. $i^{th}$ Tstim represents the configurable constant length to control the length of the electrical stimulation period, within the $i^{th}$ burst. The duration of Tstim can be between 2 and 30 minutes. Off-ramp represents the configurable negative slope to control the power of the electrical stimulation when the device starts to reduce its stimulation of the vestibular system. The duration of Off-ramp can be between 1 and 60 seconds. Tpause represents the configurable constant length to control the period that the electrical stimulation is inactive and no additional stimulation windows can be generated. The duration of Tpause can be between 5 and 240 minutes.
Figure 5:
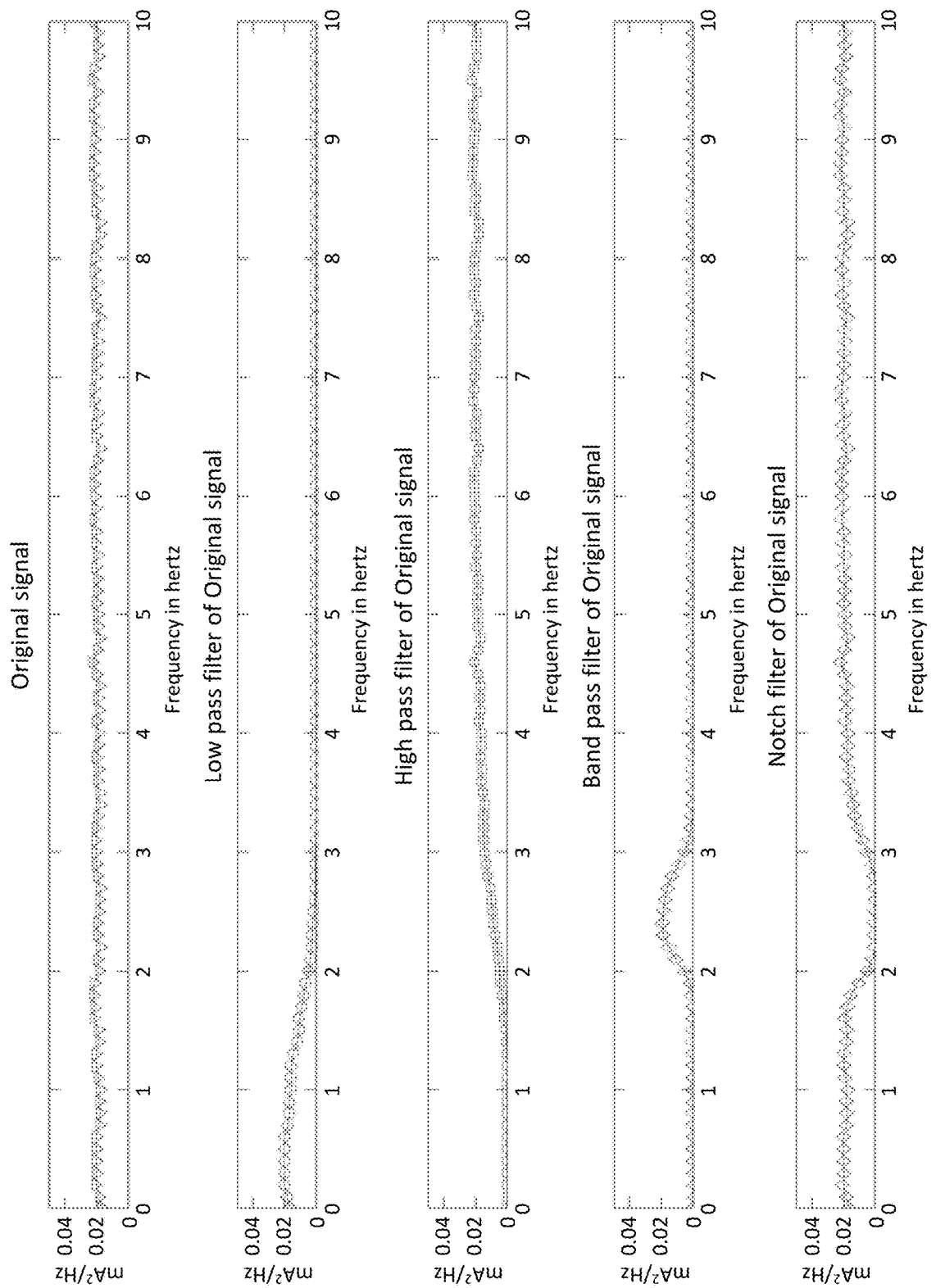
FIG. 5 depicts exemplary frequency content of the electrical signals that can be delivered to a wearer of an exemplary device.

In various embodiments, balance correction and maintenance is further controlled by the firing rate, firing intensity, duration, and firing pattern of the several electrodes 18. For example, electrodes 18 can generate electrical stimulation signals between 0.01 and 1 mA, such as 0.7 mA (FIG. 2, FIG. 3). The intensity level can be controlled automatically or by a user, such as through a wireless connection to a phone or computer. Signals can include a configurable On-ramp and Off-ramp section. For example, in FIG. 4, the On-ramp represents a period between 1 and 60 seconds wherein the power of electrical stimulation is increased to a desired level. The electrical stimulation is maintained during Tstim, a period that can range between 2 and 30 minutes. The Off-ramp represents a period between 1 and 60 seconds wherein the power of electrical stimulation is decreased to zero. Tpause represents a period that can range between 5 and 240 minutes wherein electrical stimulation is inactive. Within those ranges, several signal types are possible, including stochastic stimulation (Gaussian white noise, filtered noise including low pass, band pass, bandstop, high pass, notch pass filters) and periodic stimulation (configurable DC offset, frequency, and amplitude) (FIG. 5).

Accelerometer 24 is capable of tracking the rate of linear movement of a user along one axis, two axes, or three axes, as well as the user's orientation with respect to the constant acceleration of the gravitational field vector. Gyroscope 26 is capable of tracking the rate of rotational movement of a user around one axis, two axes, or three axes. Magnetometer 28 is capable of tracking the direction a user is facing. Combining readings from one or more of accelerometer 24, gyroscope 26, and magnetometer 28 enables device 10 to provide a number of useful data, including but not limited to a user's gait speed, head rotation angles, upper body inclination angles, stability of movement, orientation, location, and the like. Wireless transceiver 22 can be any suitable transceiver for wirelessly transmitting and receiving signals, including one or more of a Bluetooth transceiver, WiFi transceiver, near field communication transceiver, mobile transceiver (e.g., 3G, 4G, etc.), and the like. Battery 30 can be any suitable battery, such as a rechargeable battery or a replaceable battery. Embodiments comprising a rechargeable battery 30 can further comprise one or more features to enable recharging, such as a cable port for connecting to a power source. In certain embodiments, recharging is performed wirelessly by way of one or more inductive charging coils 32. In various embodiments, device 10 can further include any number of sensors, including temperature sensors, barometric pressure sensors, light sensors, biometric sensors, and the like. The one or more components described above can be integrated in frame 12, temple 14, or any combination thereof.

As described above, processor 20 and memory 21 are electrically connected to electrode 18, wireless transceiver 22, accelerometer 24, gyroscope 26, magnetometer 28, and battery 30. Processor 20 and memory 21 may operate in conjunction with a local or remote executable software platform, or with a hosted internet or network program or portal. As contemplated herein, any computing device as would be understood by those skilled in the art may be used with processor 20 and memory 21, including desktop or mobile devices, laptops, desktops, tablets, smartphones, or other wireless digital/cellular phones, televisions or other thin client devices as would be understood by those skilled in the art. Processor 20 may comprise one or more logic cores. In some embodiments, processor 20 may comprise more than one discrete integrated circuit Processor 20, in conjunction with the several components of device 10, is fully capable of sending, receiving, and interpreting device signals as described herein. For example, processor 20 can be configured to control electrode 18 parameters such as voltage, current, frequency, intensity, amplitude, period, wavelength, pulsing, and the like. Processor 20 can also be configured to monitor and record signals observed by accelerometer 24, gyroscope 26, and magnetometer 28 to memory 21. Processor 20 can be configured to record some or all of the received signals from onboard components to memory 21 and subsequently interpret the signals. Processor 20 can also be configured to record received signals from wireless transceiver 22 to memory 21 and subsequently interpret the signals. Signals can also be recorded to cloud storage. Processor 20 may be configured to interpret the various signals as a series of data points and subsequently transmit the data points to a digital display. Processor 20 may further perform automated calculations based on the various signals to output information such as velocity, acceleration, orientation, angle, location, and the like, depending on the type of signals received.

Processor 20 may further provide a means to communicate the received signals and data outputs, such as by projecting one or more static or moving images on a screen, emitting one or more auditory signals, presenting one or more digital readouts, providing one or more light indicators, providing one or more tactile responses (such as vibrations), and the like. For example, certain received signals and data outputs may indicate a user has fallen and is unable to recover, whereupon processor 20 may present one or more signals remotely to communicate the user's status and need for assistance. In some embodiments, processor 20 communicates received signals and data outputs in real time. In some embodiments, processor 20 automatically adjusts electrode 18 parameters based upon the received signals and data outputs. For example, processor 20 receiving signals and data outputs indicating a user is leaning too far in the direction of one temple tip 16 containing an electrode 18 may automatically adjust the electrode 18 to provide cathodal stimulation and adjust the electrode 18 in the opposite temple tip 16 to provide anodal stimulation, inducing the user's vestibular system response to provoke a proper postural correction.

The devices of the present invention can be made using any suitable method known in the art. The method of making may vary depending on the materials used. For example, devices substantially comprising a metal may be milled from a larger block of metal or may be cast from molten metal. Likewise, devices substantially comprising a plastic or polymer may be milled from a larger block or injection molded. In some embodiments, the devices may be made using 3D printing or other additive manufacturing techniques commonly used in the art.

In some aspects of the present invention, software executing the processor functions and instructions provided herein may be stored on a non-transitory computer-readable medium, wherein the software performs some or all of the steps of the present invention when executed on a processor. The invention thereby encompasses systems comprising software and the devices 10 described elsewhere herein.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A galvanic vestibular stimulation device, comprising:
   a glasses frame, two temples having proximal and distal ends, connected at the proximal ends to the glasses frame, and two temple tips at the distal ends of the two temples;
   one or more electrodes positioned in the temple tips;
   one or more wireless transceivers positioned in the temples;
   one or more accelerometers positioned in the temples;
   one or more gyroscopes positioned in the temples;
   one or more magnetometers positioned in the temples;
   one or more processors communicatively connected to the electrodes, the wireless transceivers, the accelerometers, the gyroscopes, and the magnetometers, the processor positioned in the temples, wherein the processors are configured to modulate a stimulation provided by the electrodes based on information provided by at least one of the accelerometers, the gyroscopes and the magnetometers; and
   one or more batteries positioned in the temples;
   wherein the one or more electrodes is configured to provide an electrical stimulation with an intensity of 0.01 to 1 mA, an increasing period of 1 to 60 seconds, a stimulation period of 2 to 30 minutes, a decreasing period of 1 to 60 seconds, and an inactive period of 5 to 240 minutes.

2. The device of claim 1, wherein one or more of the accelerometers, gyroscopes, and magnetometers communicate with the one or more processors to send information relating to the device's speed, acceleration, orientation, location, and direction.

3. The device of claim 2, wherein the one or more processors adjusts the level of the stimulation to the one or more electrodes to increase, decrease, or maintain electrode firing rate based on the received information.

4. The device of claim 1, wherein the temple tips are curved inwards towards each other.

5. The device of claim 1, wherein the one or more electrodes deliver stochastic electrical stimulation to a user's skin near the user's mastoid process to enhance postural response.

6. The device of claim 1, wherein the device sends, stores, and receives signals from cloud storage.

7. The device of claim 1, wherein the device sends, stores, and receives signals to an onboard non-transitory computer-readable storage media.

8. The device of claim 1, wherein the one or more wireless transceivers are selected from the group consisting of: Bluetooth transceiver, WiFi transceiver, near field communication transceiver, and mobile transceiver.

9. The device of claim 1, wherein the one or more batteries are rechargeable.

10. The device of claim 1, wherein the one or more batteries are removable.

11. The device of claim 1, further comprising one or more inductive charging coils positioned in the glasses frame.

12. The device of claim 1, further comprising corrective lenses or non-corrective lenses.

13. A system for galvanic vestibular stimulation, comprising:

a glasses frame, two temples having proximal and distal ends, connected at the proximal ends to the glasses frame, two temple tips positioned at the distal ends of the temples, one or more electrodes positioned in the temple tips, one or more wireless transceivers positioned in the temples, one or more accelerometers positioned in the temples, one or more gyroscopes positioned in the temples, one or more magnetometers positioned in the temples, one or more processors positioned in the temples, and one or more batteries positioned in the temples; and one or more non-transitory computer-readable media with instructions stored thereon;

wherein the instructions, when executed by the one or more processors, determine speed, acceleration, orientation, location, and direction of the glasses frame based on information provided by at least one of the accelerometers, the gyroscopes and the magnetometers, and modulates a level of stimulation at the one or more electrodes; and wherein the one or more electrodes is configured to provide an electrical stimulation with an intensity of 0.01 to 1 mA, an increasing period of 1 to 60 seconds, a stimulation period of 2 to 30 minutes, a decreasing period of 1 to 60 seconds, and an inactive period of 5 to 240 minutes.

14. The system of claim 13, wherein the one or more electrodes deliver stochastic electrical stimulation to a user's skin near the user's mastoid process to enhance postural response.

15. The system of claim 13, wherein the one or more wireless transceivers are selected from the group consisting of: Bluetooth transceiver, WiFi transceiver, near field communication transceiver, and mobile transceiver.

16. The system of claim 13, wherein the one or more batteries are rechargeable or removable.

17. The system of claim 13, further comprising one or more inductive charging coils positioned in the glasses frame.

18. The system of claim 13, further comprising corrective lenses or non-corrective lenses.

* * * * *